United States Patent [19]
Fahnenstich et al.

[11] 3,980,665
[45] Sept. 14, 1976

[54] OPTICALLY ACTIVE SALT OF PROTECTED D-PENICILLAMINE AND L-LYSINE

[75] Inventors: Rudolf Fahnenstich, Mombris; Joachim Heese; Heribert Offermanns, both of Grossauheim, all of Germany

[73] Assignee: Deutsche Gold- und Silber-Scheideanstalt vormals Roessler, Germany

[22] Filed: Jan. 25, 1974

[21] Appl. No.: 436,743

[30] Foreign Application Priority Data
Jan. 27, 1973 Germany.............................. 2304054

[52] U.S. Cl.................. 260/306.7 C; 260/326 S; 260/455 R; 260/456 A; 260/501.12; 260/534 S

[51] Int. Cl.².................................... C07D 277/06

[58] Field of Search............... 260/306.7 C, 534 S, 260/534 L, 501.12, 326 S, 455 R, 456 A

[56] References Cited
UNITED STATES PATENTS

| | | | |
|---|---|---|---|
| 2,450,784 | 10/1948 | Duffin et al................. | 260/306.7 C |
| 2,539,854 | 1/1951 | Mozingo et al.................. | 260/534 S |
| 2,865,928 | 12/1958 | Fielos et al...................... | 260/534 L |
| 3,845,110 | 10/1974 | Fahnenstich et al........... | 260/501.12 |

OTHER PUBLICATIONS
Asinger et al., Chem. Abstracts, 79:146846h (1/29/73).

*Primary Examiner*—Richard J. Gallagher
*Attorney, Agent, or Firm*—Cushman, Darby & Cushman

[57] ABSTRACT
D,L-penicillamine is converted to D-penicillamine with the aid of L-lysine.

14 Claims, No Drawings

OPTICALLY ACTIVE SALT OF PROTECTED D-PENICILLAMINE AND L-LYSINE

The amino acid D-penicillamine is known to be an important medicine for the treatment of Morbus Wilson, defective schizophrenia, scleroderma, cystinuria and chronic agressive hepatitis as well as basic therapy of primary chronic polyarthritis. D-penicillamine is also useful as an antidote for heavy metal intoxications. Therapeutic uses are only found for D-penicillamine since the L-isomer is much more toxic.

It is known to recover D-penicillamine in an expensive, hydrolytic process from the highly expensive starting material, penicillin. The D-penicillamine produced in this way is so expensive that it cannot be used for broad medicinal purposes, especially as a basic therapeutic for long lasting treatment of primary chronic polyarthritis. For this reason, a total synthesis of D-penicillamine is of special significance.

It is also known, however, to produce D,L-penicillamine synthetically and to recover the D-penicillamine by splitting the racemate. As optically active bases for this purpose there have been used d-pseudoephedrine and l-ephedrine (see "The Chemistry of Penicilline" (1949) Princeton University Press; British Pat. No. 585,413 and corresponding Duffin U.S. Pat. No. 2,450,784, and Belgian Pat. No. 738,520).

For the racemate splitting, the D,L-penicillamine must be converted into suitable derivatives, that is, protective groups must be introduced into the penicillamine molecule, as is customary in the racemate splitting of amino acids. Suitable derivatives for the racemate splitting for example are the N-acylated products of D,L-penicillamine or of S-benzyl-D,L-penicillamine as well as the acylation product of the reaction product of D,L-penicillamine with carbonyl compounds.

These processes for the racemate splitting of D,L-penicillamine, however, are only slightly satisfactory since in the reaction of the D,L-penicillamine derivatives with the above-named splitting bases the undesired salt of the L-penicillamine derivative and the optically active base precipitates. It is known, however, that on principle the antipode crystallizing out of the reaction mixture has the higher purity (H. D. Jakubke and H. Jeschkeit, "Aminosauren, Peptide, Proteine", Akademie-Verlag, Berlin, 1969, as well as L. F. Fieser and M. Fieser, "Lehrbuch der Organischen Chemie", Verlag Chemie, Weinheim, 1957).

It has now been found that it is especially advantageous to use L-lysine as the optically active base for the recovery of D-penicillamine from D,L-penicillamine. The splitting of the racemate of D,L-penicillamine proceeds with the help of this optically active base with very high yields. The D-penicillamine is obtained in high purity since the desired salt of the D-acid and the L-base is the very much more difficultly soluble diastereomeric salt and precipitates.

As in the known processes for racemate splitting also in the process of the present invention the D,L-penicillamine must first be converted into a suitable derivative for the racemate splitting before the reaction with the L-lysine can take place. At least one of the hydrogen atoms of the amino group must first be protected. At the same time the hydrogen atom of the mercapto group can be protected. For the protection of the hydrogen atom or atoms there can be used any of the known methods, such as those described in "Chemistry of the Aminoacids", J. P. Greenstein and M. Winitz, J. Wiley and Sons, Inc., New York, 1961; as well as in Houben Weyl, 1958, Vol. 11, part 2, Georg Thieme Verlag. Such protection can be obtained for example if D,L-penicillamine is converted in known manner to a compound having the formula:

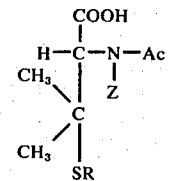

in which Ac is an acyl group, especially benzoyl, tosyl, nitrophenyl sulfenyl, lower alkanoyl, e.g., acetyl or preferably formyl, Z is hydrogen or together with Ac can be a diacyl group, especially phthaloyl and R is hydrogen or benzyl or can have the same meaning as Ac. Examples of such compounds include D,L-N-formyl penicillamine, D,L-N-acetyl penicillamine, D,L-N-propionyl penicillamine, D,L-N-benzoyl penicillamine, D,L-N-tosyl penicillamine, D,L-nitrophenyl sulfenyl penicillamine, D,L-N-phthaloyl penicillamine, D,L-N-formyl-S-benzyl penicillamine, D,L-N-acetyl-S-benzyl penicillamine, D,L-N-propionyl-S-benzyl penicillamine, D,L-N-benzoyl-S-benzyl penicillamine, D,L-N-tosyl-S-benzyl penicillamine, D,L-N-nitrophenylsulfenyl-S-benzyl penicillamine, D,L-N-phthaloyl-S-benzyl penicillamine, D,L-N-formyl-S-formyl penicillamine, D,L-N-formyl-S-acetyl penicillamine, D,L-N-formyl-S-benzoyl penicillamine, D,L-N-formyl-S-tosyl penicillamine, D,L-N-formyl-S-nitrophenyl-sulfenyl penicillamine, D,L-N-phthaloyl-S-benzyl penicillamine, D,L-N-acetyl-S-formyl penicillamine, D,L-N-formyl-S-formyl penicillamine, D,L-N-phthaloyl-S-propionyl penicillamine, D,L-N-acetyl-S-benzoyl penicillamine, D,L-N-formyl-S-tosyl penicillamine, D,L-N-formyl-S-nitrophenylsulfenyl penicillamine.

Preferably, however, the protection of such groups is provided by converting the D,L-penicillamine in known manner into a thiazoline-4-carboxylic acid of the formula:

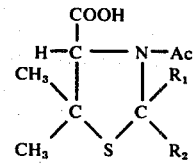

in which $R_1$ and $R_2$ are the same or different and are hydrogen, alkyl of 1 to 8 carbon atoms, cycloalkyl with 5 to 8 carbon atoms or aryl, i.e., for example benzyl or $R_1$ and $R_2$ together with the adjacent carbon atom form a cycloalkyline ring, e.g., of 5, 6, 7 or 8 carbon atoms and Ac is an acyl group, especially benzoyl, tosyl, nitrophenylsulfenyl, lower alkanoyl, e.g., acetyl or preferably formyl.

Of these protected compounds there are preferred those in which the D,L-penicillamine is converted into an N-acetyl or, preferably N-formyl derivative of a 2,2-dialkyl-5,5-dimethyl thiazolidine-4-carboxylic acid. Of these there is preferred 3-formyl-2,2,5,5-tetramethyl-thiazolidine-4-carboxylic acid (N-formylisopropylidene-D,L-penicillamine) or 3-formyl-2,2-pentamethylene-5,5-dimethyl-thiazolidine-4-carboxylic acid. These thiazolidine-4-carboxylic acids can be made in a simple manner from D,L-penicillamine and the corresponding carboxylic compounds (The Chemistry of Penicilline (1949), Princeton University Press). The conversion into the N-acyl compounds as well as the compounds with protected mercapto groups is described in the same literature.

Other thiazolidine-4-carboxylic acids which can be used and which are within formula II include D,L-3-acetyl-2,2,5,5-tetramethyl-thiazolidine-4-carboxylic acid, D,L-3-propionyl-2,2,5,5-tetramethyl thiazolidine-4-carboxylic acid, D,L-3-benzoyl-2,2,5,5-tetramethyl-thiazolidine-4-carboxylic acid, D,L-3-p-toluenesulfenyl-2,2,5,5-tetramethyl-thiazolidine-4-carboxylic acid, D,L-3-p-nitrophenylsulfenyl-2,2,5,5-tetramethyl-thiazolidine-4-carboxylic acid, D,L-3-formyl-2,2-diethyl-5,5-dimethyl-thiazolidine-4-carboxylic acid, D,L-3-formyl-2,2-hexamethylene-5,5-dimethyl-thiazolidine-4-carboxylic acid, D,L-3-formyl-2,2-dioctyl-5,5-dimethyl-thiazolidine-4-carboxylic acid, D,L-3-formyl-2,2-dibutyl-5,5-dimethyl-thiazolidine-4-carboxylic acid, D,L-3-formyl-2,2-dicyclohexyl-5,5-dimethyl-thiazolidine-4-carboxylic acid, D,L-3-formyl-2,2-dicyclopentyl-5,5-dimethyl-thiazolidine-4-carboxylic acid, D,L-3-formyl-2,2-diphenyl-5,5-dimethyl-thiazolidine-4-carboxylic acid, D,L-3-formyl-2,2-di-o-tolyl-5,5-dimethyl-thiazolidine-4-carboxylic acid, D,L-3-acetyl-2,2-dihexyl-5,5-dimethyl-thiazolidine-4-carboxylic acid.

For the recovery of the D-penicillamine according to the process of the invention there is generally used as starting material isomeric mixtures containing D-penicillamine which contain the optically active components in equal parts, especially those prepared synthetically as racemates. However, there also can be used isomeric mixtures in which the components are present in different molar proportions.

The fractional crystallization for separation of the diastereomeric salts formed from the protected penicillamine and the L-lysine is advantageously carried out in alcoholic solution. As alcohols there are preferably used lower alkanols such as methanol, ethanol, propanol, and isopropanol. There can also be used mixtures of alcohols with other solvents such as ethers, e.g., diethyl ether, dipropyl ether, dibutyl ether, dimethyl ether, ketones, e.g., acetone, methyl ethyl ketone, methyl butyl ketone, and diethyl ketone, and water. The amount of water should not be over 10%. The lower alkanol usually has 1 to 3 carbon atoms, but this can be higher, e.g., 4, 5 or 6 carbon atoms, e.g., butanol, pentanol, hexanol, sec. butyl alcohol.

The formation of stereoisomeric salts generally takes place without doing anything further in the successive solution of the protected D,L-penicillamine and then the L-lysine in the alcoholic solvent. This is suitably held at temperatures between 20° and 60° C. The L-lysine for the most part is used as the free base; in a given case it can also be used as a salt, for example, the hydrochloride, hydrobromide, sulfate, etc. For each mole of isomeric mixture there is suitably added about 0.5 to 1.5 moles, especially 1.0 to 1.2 moles of L-lysine. The desired salt of L-lysine and the protected D-isomer of the penicillamine generally crystallizes out spontaneously upon cooling the alcoholic solution. In many cases, however, it is necessary to inoculate the solution. For this purpose there is used the most highly pure possible fraction of the salt to be crystallized out in amounts between about 0.1 and 20%, especially between 5 and 15% based on the total content of the diastereomeric salt of the solution. The crystallization is generally carried out with advantage at temperatures between about −20° and +40° C. If necessary to increase the optical purity, the crystallizate is recrystallized or digested in warm alcohol.

In each case there precipitates first in the racemate splitting the more difficultly soluble salt of the D-penicillamine derivative and L-lysine while the other diastereomer remains in solution. This was completely surprising since in the use of both D-pseudophedrine and 1-ephedrine the salt of the L-penicillamine derivative and the splitting base is more difficultly soluble.

The splitting of the more difficultly soluble salt likewise occurs in known manner through treatment with preferably aqueous mineral acids, for example dilute hydrochloric acid (or hydrobromic acid, sulfuric acid or nitric acid), whereby besides the D-penicillamine derivative the L-lysine is recovered in the form of the mineral acid salt.

The splitting of the D-penicillamine derivative likewise takes place in known manner by splitting off the protective group, for example debenzylation or acid hydrolysis.

In an analogous manner L-penicillamine can be recovered from the mother liquor of the splitting of the racemate. It is especially advantageous, however, to racemize in known manner the L-penicillamine derivative *), whereby it is possible to recycle the therapeutically nonusable L-penicillamine.

*) which is in a given case prepared by splitting the salt with a dilute mineral acid Unless otherwise indicated all parts and percentages are by weight.

In the following examples, the rotatory power of the materials is always given as specific rotation $[\alpha]_D^{20}$ in degrees . cm$^3$/dm . g.

EXAMPLE 1

32.1 grams of L-lysine and 43.8 grams of D,L-3-formyl-2,2,5,5-tetramethyl-thiazolidine-4-carboxylic acid were dissolved in 240 ml of methanol at 25° C. The solution was cooled to 0° C. with stirring and inoculated with 3.6 grams of an optically pure salt of L-lysine and D-3-formyl-2,2,5,5-tetramethyl-thiazolidine-4-carboxylic acid. After 3 hours the precipitated crystals were filtered off with suction; it was washed twice with 30 ml (each time) of cold methanol and then dried at 40° C. under reduced pressure. The yield of salt was 23.7 grams, corresponding to 59%. The salt had an optical rotation of +50°, which corresponds to an optical purity of 94%. (A salt produced from pure components had an optical rotation of 53.5°).

14.5 grams of the salt of L-lysine and D-3-formyl-2,2,5,5-tetramethyl-thiazolidine-4-carboxylic acid recovered was dissolved in 50 ml of water and treated with 8 ml of 6 normal hydrochloric acid. The precipitate formed was filtered off with suction, washed with water and dried. There were obtained 7.45 grams of D-3-formyl-2,2,5,5-tetramethyl-thiazolidine-4-carboxylic acid. This had an optical rotation of +54° (concentration = 1 gram/100 ml in methanol). The D-3-formyl-2,2,5,5-tetramethyl-thiazolidine-4-carboxylic acid was mixed with 45 ml of 15% hydrochloric acid which was heated to 70° C. The mixture was held for 2 hours at 70° C. with distillation of acetone and then brought to dryness in a rotatory evaporator. There were recovered 5.04 grams of crude D-penicillamine hydrochloride.

The D-penicillamine hydrochloride was dissolved in 40 ml of 96% ethanol, the solution treated with 29.5 grams of triethyl amine, whereupon the free D-penicillamine precipitated. It was filtered off with suction, washed with 96% ethanol and dried under reduced pressure at 50° C. The D-penicillamine had an optical rotation of −62° and a melting point of 182° to 184° C. The yield was 3.6 grams.

By evaporation of the mother liquor remaining in the crystallization of the salt of L-lysine and D-3-formyl-2,2,5,5-tetramethyl-thiazolidine-4-carboxylic acid there were recovered a salt of L-lysine and substantially L-3-formyl-2,2,5,5-tetramethyl-thiazolidine-4-carboxylic acid. From this there was separated L-lysine by treatment with dilute hydrochloric acid. The L-3-formyl-2,2,5,5-tetramethyl-thiazolidine-4-carboxylic acid was racemized by heating in toluene in the presence of acetic anhydride.

EXAMPLE 2

16.1 grams of L-lysine and 21.9 grams of D,L-3-formyl-2,2,5,5-tetramethyl-thiazolidine-4-carboxylic acid were dissolved in 150 ml of methanol at room temperature. The solution was cooled to 0° C. with stirring and inoculated with 0.1 gram of an optically pure salt of L-lysine and D-3-formyl-2,2,5,5-tetramethyl-thiazolidine-4-carboxylic acid. After 5 hours the precipitated crystals were filtered off. They had an optical purity of 80%. The yield was 10 grams. The crystals were then dissolved in 50 ml of methanol at 50° C. The solution was cooled to 0° C. and treated with 0.1 gram of the same inoculating salt. After one hour the precipitated crystals were filtered off with suction, washed with 10 ml of methanol and dried at 40° C. under reduced pressure. There were recovered 7.1 grams of the salt of L-lysine and D-3-formyl-2,2,5,5-tetramethyl-thiazolidine-4-carboxylic acid. This had an optical purity of 100%. The D-penicillamine recovered therefrom in the manner described in example 1 in a yield of 1.8 grams had an optical rotation of −62.8° and a melting point of 212° to 214° C.

EXAMPLE 3

39.5 grams of a salt of L-lysine and D-3-formyl-2,2,5,5-tetramethyl-thiazolidine-4-carboxylic acid with an optical purity of 81% was suspended in 170 ml of isopropanol at 60° C. The mixture was held at this temperature for 60 minutes with stirring and then filtered at this temperature. The residue recovered was washed twice, each time with 30 ml of isopropanol, at 60° C. and then dried under reduced pressure at 40° C. The yield amounted to 34.6 grams, corresponding to 88%. The salt recovered from L-lysine and D-3-formyl-2,2,5,5-tetramethyl-thiazolidine-4-carboxylic acid had an optical purity of about 90%. The D-penicillamine recovered therefrom in the manner described in example 1 had an optical purity of 98.5%. The yield was 9.3 grams.

What is claimed is:

1. The optically active salt of a protected D-form of penicillamine and L-lysine where the protected penicillamine has the formula

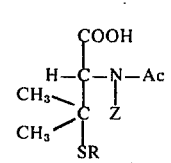

where Ac is benzoyl, tosyl, nitrophenyl-sulfenyl, formyl, acetyl or propionyl, R is hydrogen, benzyl or Ac, $R_1$ and $R_2$ are hydrogen, alkyl of 1 to 8 carbon atoms, cycloalkyl of 5 to 8 carbon atoms, phenyl or tolyl or $R_1$ and $R_2$ together with the adjacent carbon atoms of the thiazoline ring form a cycloalkylene ring of 5 to 8 carbon atoms and Z is hydrogen or together with Ac is phthaloyl.

2. The optically active salt according to claim 1 having formula II wherein Ac is acetyl or formyl and $R_1$ and $R_2$ are each methyl.

3. A compound according to claim 1 having formula I.

4. A compound according to claim 3, wherein Ac is formyl, acetyl or propionyl and Z is hydrogen.

5. A compound according to claim 4 wherein Ac is formyl.

6. A compound according to claim 5 wherein R is benzyl.

7. A compound according to claim 1 having formula II.

8. A compound according to claim 7 wherein $R_1$ and $R_2$ are alkyl of 1 to 8 carbon atoms, cycloalkyl of 5 to 8 carbon atoms, phenyl or tolyl or $R_1$ and $R_2$ together with the adjacent carbon atoms are cycloalkylene of 5 to 8 carbon atoms.

9. A compound according to claim 8 wherein Ac is formyl acetyl or propionyl.

10. A compound according to claim 8, wherein Ac is formyl or acetyl and $R_1$ and $R_2$ are both alkyl.

11. A compound according to claim 10 wherein Ac is formyl.

12. A compound according to claim 11 wherein $R_1$ and $R_2$ are both methyl.

13. A compound according to claim 8 wherein $R_1$ and $R_2$ together with the adjacent carbon atom is cycloalkylene of 5 to 8 carbon atoms.

14. A compound according to claim 13 wherein Ac is formyl or acetyl and the cycloalkylene is cyclopentamethylene.

* * * * *